United States Patent [19]

Gerstenberger et al.

[11] Patent Number: 4,995,150

[45] Date of Patent: Feb. 26, 1991

[54] METHOD AND APPARATUS FOR MAKING FEMININE HYGIENIC INTERLABIA PADS

[75] Inventors: Roland W. Gerstenberger, Arden; Philip E. Cantrell, Hendersonville, both of N.C.

[73] Assignee: Xtramedics, Inc., Deerfield, Ill.

[21] Appl. No.: 488,989

[22] Filed: Mar. 5, 1990

[51] Int. Cl.⁵ .................... D04H 1/22; A61F 13/20
[52] U.S. Cl. .................................. 28/119; 28/118; 604/385.1; 604/904
[58] Field of Search ............... 28/118, 119; 604/385.1, 604/904

[56] References Cited

U.S. PATENT DOCUMENTS

| | | | |
|---|---|---|---|
| 2,566,190 | 8/1951 | Greiner et al. | 604/904 X |
| 3,547,930 | 12/1970 | Blomqvist et al. | 604/385.1 X |
| 3,983,873 | 10/1976 | Hirschman | 604/385.1 |
| 4,095,542 | 6/1978 | Hirschman | 112/262.3 |
| 4,142,476 | 3/1979 | Hirschman | 112/262.2 |
| 4,294,253 | 10/1981 | Friese | 604/385.1 |
| 4,627,849 | 12/1986 | Walton et al. | 604/385.1 X |
| 4,743,237 | 5/1988 | Sweere | 604/904 X |

Primary Examiner—Werner H. Schroeder
Assistant Examiner—Bradley Kurtz De Sandro
Attorney, Agent, or Firm—David M. Carter

[57] ABSTRACT

There is provided a method and apparatus for manufacturing feminine hygienic pads in the form of adjacent thick and thin elongated panels having a filler of absorbent material and an outer covering. A rope of absorbent material and a web of the outer covering are brought together in a die. The die in the form of a hollow tube and a tapered guide causes the outer covering to enclose the absorbent material with the seam for the outer covering being on the inside of the pad. The adjacent panels are formed by sewing the pad.

14 Claims, 4 Drawing Sheets

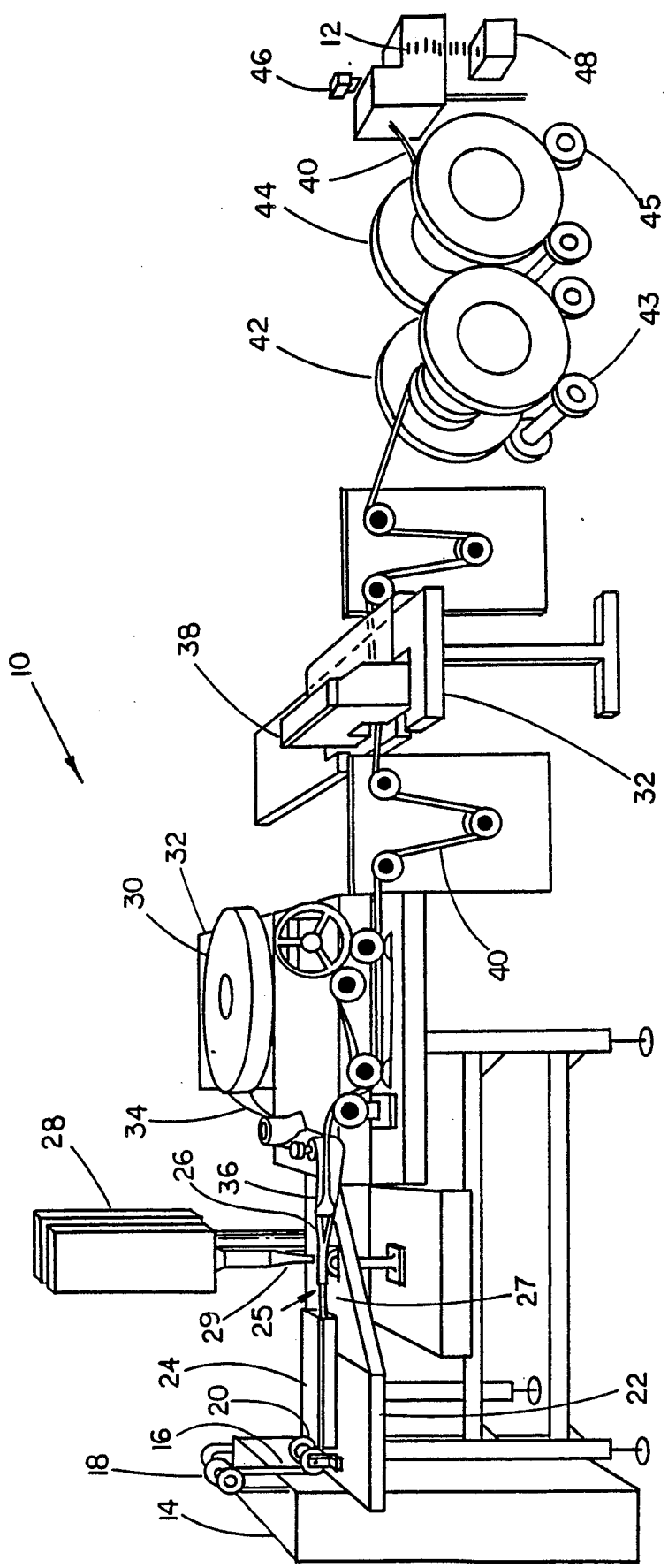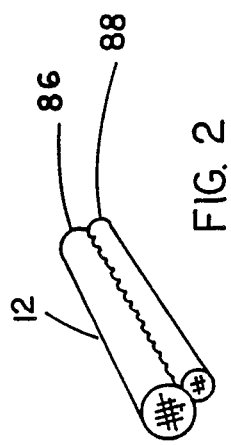

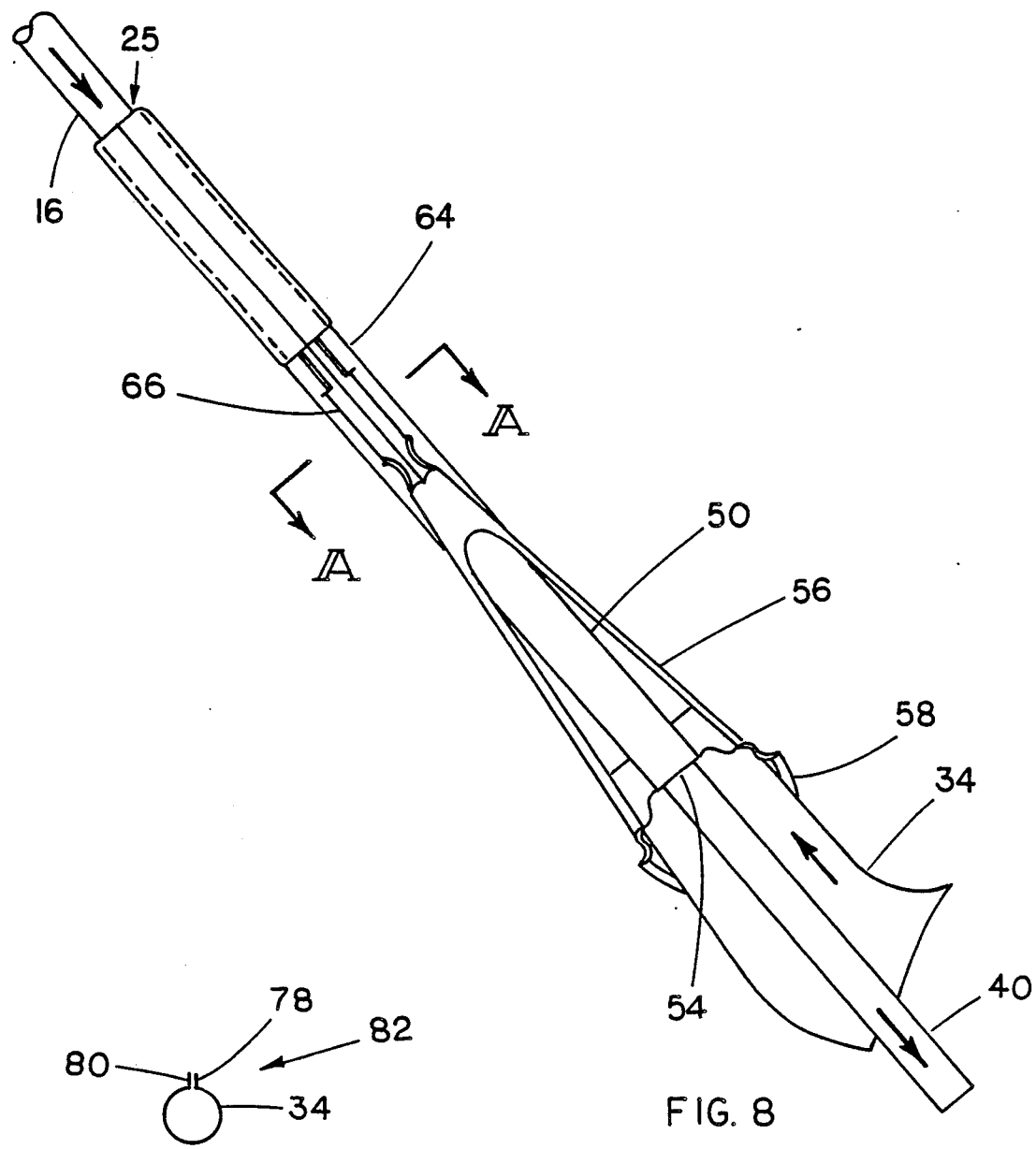
FIG. 8
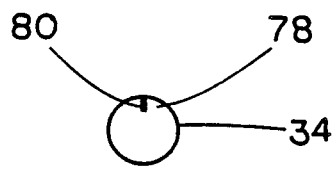
FIG. 9
FIG. 10

4,995,150

METHOD AND APPARATUS FOR MAKING FEMININE HYGIENIC INTERLABIA PADS

BACKGROUND OF THE INVENTION

This invention relates to methods and apparatus for manufacturing absorbent pads. More particularly, it relates to methods and apparatus for manufacturing feminine hygienic pads.

Feminine hygienic pads consisting of various layers of absorbent materials are used primarily to absorb uncontrolled discharges during menstruation. These pads have taken the form of thick elongated feminine napkins which are primarily used during the early stages of the menstrual cycle and narrow absorbent tubes, known as tampons, which are inserted into the vagina and which are used primarily during the latter stages of the menstrual cycle.

A third type of feminine hygienic pad known as the interlabia pad has been developed by Xtramedics, Inc., assignee of the subject invention. Various forms of interlabia pads as well as methods of producing the same are described in U.S. Pat. Nos. 3,983,873, 4,095,542, and 4,142,476, all assigned or licensed to Xtramedics, Inc. The Xtramedics interlabia pads are designed to be placed longitudinally between the vaginal lips or labia and are particularly useful during light discharges of menstrual fluids, mid-cycle spotting or discharges, slight loss of urine caused by physical stress, or leakages following intercourse.

While the Xtramedics interlabia pad has met with commercial success, it is desirable to provide a manufacturing process which enables efficient, inexpensive and consistent production of the pad.

OBJECTS OF THE INVENTION

It is therefore one object of this invention to provide an improved method and apparatus for manufacturing absorbent pads.

It is another object to provide an improved method and apparatus for manufacturing interlabia absorbent pads.

It is still another object to provide a method and apparatus for manufacturing interlabia pads having dimensions and characteristics which will readily fit into the interlabia space.

It is still another object to provide a method and apparatus for manufacturing interlabia absorbent pads with a limited number of manufacturing steps and which may be made using a minimal amount of labor.

SUMMARY OF THE INVENTION

In accordance with one form of this invention, there is provided an apparatus for producing absorbent pads. The apparatus includes a first container having a supply of absorbent material in elongated rope form and a second container having a supply of outer cover material in elongated web form. A die is provided for joining the rope of absorbent material and the web as an outer cover over the absorbent material. The die includes a tube having first and second open ends. The first open end receives the rope of absorbent material and further receives the web after the web is formed into a cylindrical shape by the die. The web forms the outer cover. A mechanism is provided for sealing the elongated edges of the web. The second open end expels an elongated strand which includes the absorbent material contained within the sealed web. Preferably the strand is sewn along its longitudinal axis forming a pair of adjacent panels, one of which is much wider and thicker than the other. The strand may then be cut into desired lengths corresponding to the dimensions of the interlabia region.

In accordance with another form of this invention, there is provided a method for producing absorbent pads including the following steps: (1) moving elongated rope of absorbent material in one direction through a hollow tube; (2) moving a flat elongated web along the outside of the tube in the opposite direction from the rope of absorbent material; (3) forming the web into a substantially hollow cylindrical shape; (4) moving the formed web through the tube between the inner walls of the tube and the absorbent material in the same direction as the absorbent material; and (5) cover the, absorbent material with the cylindrical shaped web. Preferably the longitudinal edges of the web are sealed on the inside of the formed hollow cylinder. The absorbent material and sealed web are then passed out of the tube and the resulting elongated strand may then be cut to appropriate dimensions.

BRIEF DESCRIPTION OF THE DRAWINGS

The subject matter which is regarded as the invention is set forth in the appended claims. The invention itself, however, together with further objects and advantages thereof may be better understood in reference to the accompanying drawings in which:

FIG. 1 is a diagram of apparatus which may be used in carrying out the subject invention.

FIG. 2 is a pictorial view of an absorbent pad produced by the apparatus of FIG. 1.

FIG. 8 is a top view of the apparatus of FIG. 3 showing the operation of such apparatus.

FIG. 9 is a sectional view of the web of material as it passes over the outside of the tube of FIG. 8 taken through lines A—A.

FIG. 10 is a sectional view of the web material as it passes through the inside of the tube of FIG. 8 taken through lines A—A.

DESCRIPTION OF THE PREFERRED EMBODIMENT

Figures 3, 4:
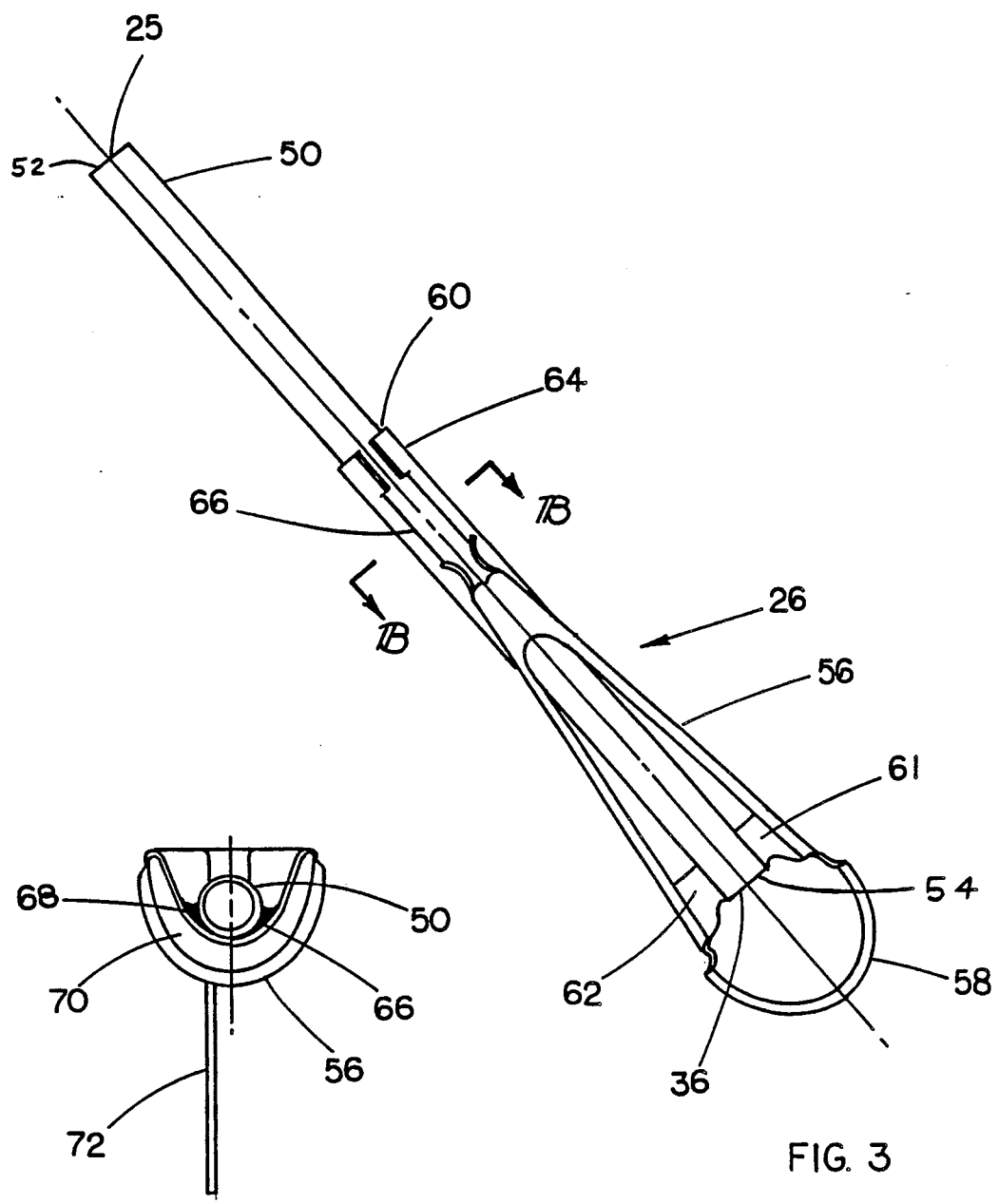
FIG. 3 is a top view of a die forming part of the apparatus of FIG. 1.
FIG. 4 is a rear elevational view of one end of the die shown in FIG. 3.

Referring now more particularly to FIG. 1, there is shown apparatus 10 useful for producing the interlabia absorbent pad 12 shown in FIG. 2. Drum 14 contains a quantity of absorbent material which is in the form of elongated rope 16. Preferably the absorbent material is made of rayon fiber. Guide roller 18 is connected to the top of container 14 for guiding the rope out of the container. Guide roller 20 is mounted on table 22 and guides the absorbent rope 16 through housing 24 and into the open front portion 25 of die 26. Ultrasonic welder 28 is mounted above die 26. Payoff reel 30 is mounted on table 32 and contains elongated web material 34 which forms the outer covering of absorbent pad 12. Web 34 is received at end 36 of die 26. Sewing machine 38 is also mounted on table 32 for sewing strand 40 which is formed by the combination of the absorbent material 16 and web 34 after they are joined in die 26. Reel 42 takes up strand 40. FIG. 1 also shows a second reel 44 which is already full of the strand 40. Reel 44 becomes an unwind reel to feed the strand 40 under knife 46 for chopping the strand into short, absorbent pads 12 which are then dropped into container 48 wrapped and packaged.

Referring now more particularly to FIG. 3, die 26 includes elongated hollow tube 50 having opposing open ends 52 and 54. Die 26 also includes tapered guide 56. Portions of tube 50 are received within tapered guide 56. Tapered guide 56 is more open at its end 58 than its end 60. Beams 61 and 62 connect the taper guide to tube 50. The most narrow portion of the taper guide near end 60 forms a concentric cylinder 64 around a portion of tube 50. Rectangular hole 66 in cylinder 64 aligns with rectangular hole 76 in tube 50 as may be seen in FIG. 5. End 52 of tube 50 is for receiving the rope of absorbent material 16 as well as the web 34 after it has been formed into a cylindrical shape by the tapered guide 56. End 54 of tube 50 is for dispensing strand 40 which consists of the absorbent rope 16 and web cover 34.

Referring now more particularly to FIG. 4, tube 50 is also attached to the tapered guide 56 by welds 66 and 68. Space 70 is formed within guide 56 for receiving web 34. Bracket 72 is used to mount die 26 to table 27 shown in FIG. 1.

Figure 5:
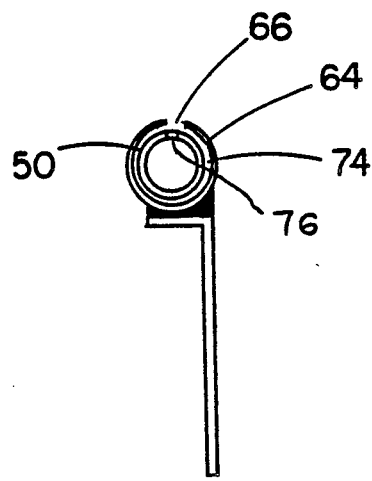
FIG. 5 is a sectional view of the die of FIG. 3 taken through lines B—B.
Figure 6:
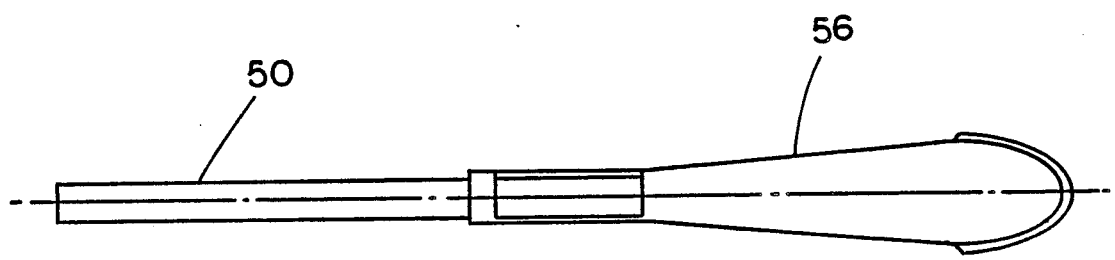
FIG. 6 is a bottom view of the apparatus of FIG. 3.
Figure 7:
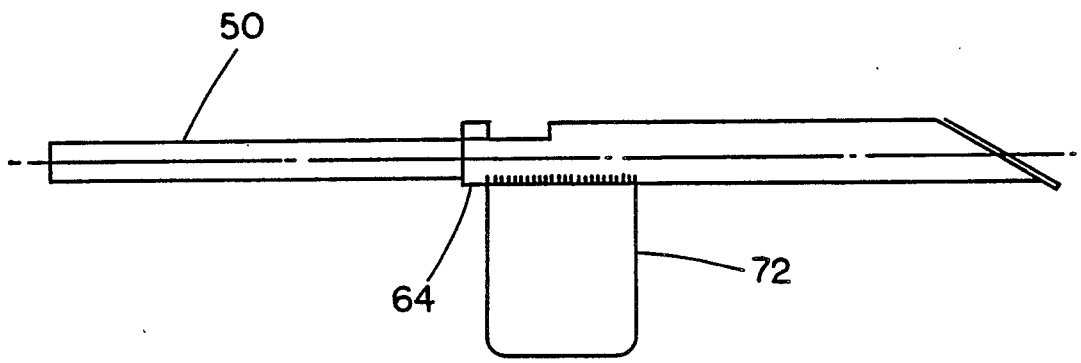
FIG. 7 is a side elevational view of the apparatus of FIG. 3.

Referring now to FIG. 5, which is a cross section of the die 26 shown in FIG. 3 taken through lines B—B, tube 50 and the narrow portions 60 of the tapered guide 56 form concentric rings with web 34 passing through space 74 created as a result of the spacing between tube 50 and cylinder 64. Slot 66 in cylinder 64 and slot 76 in tube 50 align with one another and also align with tip 29 of ultrasonic welder 28, as shown in FIG. 1, for sealing the elongated edges 78 and 80 of web 34 after the web has been formed into its tubular shape as shown in FIG. 9.

The absorbent pad 12 shown in FIG. 2 may be manufactured using the above described apparatus as set forth below. Absorbent rope 16 passes out of container 14 over roller 18 and under roller 20 and into the front opening 52 of tube 50 as shown in FIG. 8. At the same time and at the same speed, web 34 passes into the wide end 58 of tapered guide 56 and under beams 61 and 62 into space 74. The tapered guide causes the web 34 to become curved, and when web 34 reaches enclosed neck or cylinder 64, the cross section of the web forms a complete oval or circle and thus the web becomes an elongated hollow cylinder. The direction of movement of web 34 is reversed and the web is then folded inside out by passing the web 34 into opening 52 of tube 50.

The seam 82 formed by the longitudinal edges 78 and 80, which prior to the direction reversal is on the outside as shown in FIG. 9, is moved to the inside of the cylindrical shaped web as shown in FIG. 10. The web remains in tubular form and becomes located between the absorbent material and the inside walls of tube 50. The seam passes under opening 66 and 76 and thus under tip 29 of ultrasonic device 28 where the seam is heat sealed by the ultrasonic device. The outer covering web 34 is made of a heat sealable material such as polypropylene but also is liquid permeable so that fluids will pass therethrough into absorbent material 16. A strand 40 made of the web covered absorbent rope passes through open end 54 of tube 50. The strand moves to sewing machine 38 where a portion of the strand is sewn forming elongated panels 86 and 88 with panel 86 being substantially wider and thicker than panel 88. Strand 40 then proceeds to takeup reel 42. After takeup reel 42 is full, it is removed from its stand 43 and placed on stand 45 where it becomes unwind reel 44. Unwind reel 44 then passes strand 40 under knife 46 which cuts the strand into predetermined lengths to form absorbent pad 12 shown in FIG. 2.

Thus there is provided a cost effective and efficient manufacturing apparatus and process for making uniform absorbent pads shown in FIG. 2 which are particularly useful as interlabial absorbent devices. The seam is on the inside of the outer covering so that it is comfortable to the user. Furthermore, the apparatus may be operated using minimal labor without an undue number of steps and procedures.

From the foregoing description of the preferred embodiment of the invention, it will be apparent that many modifications may be made therein. It will be understood however that this embodiment of the invention is a exemplification of the invention only and that the invention is not limited thereto. It is to be understood therefore that it is intended in the appended claims to cover all modifications as fall within the true spirit and scope of the invention.

We claim:

1. An apparatus for producing absorbent pads comprising:
   a supply of absorbent material in elongated rope form;
   a supply of outer cover material in elongated web form; said web of outer cover material having parallel elongated edges;
   a die for joining said rope of absorbent material and said web of outer cover material; said die including a hollow tube; said tube having first and second open ends; said first open end receiving said rope of absorbent material and said web; means for sealing the elongated edges of said web of outer cover material; said open end of said tube expelling an elongated strand including said rope of absorbent material covered by said sealed web.

2. An apparatus as set forth in claim 1 wherein said die includes means for forming said web into an elongated hollow cylinder form.

3. An apparatus as set forth in claim 2 further including means for turning said edges of said web into the inside of said elongated hollow cylinder formed by said web.

4. An apparatus as set forth in claim 2 wherein said means for forming said web includes a tapered guide, said tube connected to said tapered guide; said tapered guide being wider near said second open end of said tube than near said first open end of said tube.

5. An apparatus as set forth in claim 4 wherein said tapered guide includes a cylindrical portion substantially surrounding a portion of said tube.

6. An apparatus as set forth in claim 3 wherein said means for sealing includes a hole in said tube and further includes heating means located near said hole.

7. An apparatus as set forth in claim 1 further including means for forming said strand into first and second adjacent panels; said first panel being wider and thicker than said second panel.

8. An apparatus as set forth in claim 7 wherein said means for forming said strands into panels includes a sewing machine; said sewing machine providing stitches between said panels.

9. A method for producing absorbent pads comprising the steps of:

moving a rope of absorbent material in one direction through the inside of a hollow tube;

moving a web of material along the outside of said hollow tube in a direction which is opposite to the direction of movement of said rope; reversing the direction of said web approximately 180°; moving said web in said reversed direction through the inside of said hollow cylinder between said rope of absorbent material and the inside walls of said hollow cylinder; covering said rope of absorbent material with said web.

10. A method as set forth in claim 9 further including the step of forming said web into hollow cylinder form.

11. A method as set forth in claim 10 further including the steps of moving the adjacent edges of said web to the inside of said cylinder formed by said web; sealing said edges of said web.

12. A method as set forth in claim 11 further including the step of expelling a strand, formed by the combination of said absorbent material and said web, out of said tube in the same direction as the movement of said rope and said web after reversal of the movement of said web; forming adjacent panels in said strand and cutting said strand; into pads having predetermined lengths.

13. A tool for forming a covered strand made from an elongated rope and an elongated web comprising:

a hollow tube having first and second open ends;

a tapered guide; said tube connected to said tapered guide; said tapered guide including a cylindrical portion surrounding a portion of said tube; said tapered guide being wider near said second end of said tube than at said cylindrical portion; said wider portion of said tapered guide receiving said elongated web and said cylindrical portion of said tapered guide for forming said web into a hollow cylinder; said first end of said tube for receiving said rope and said cylindrically shaped web; said second end of said tube for expelling said strand formed by said web and said rope.

14. A tool as set forth in claim 13 further including a first hole in said tube and a second hole in said cylindrical portion of said tapered guide; said first and second holes substantially aligning with one another whereby heat may pass through said holes for sealing the edges of said web.

* * * * *